US009386990B2

(12) United States Patent
Muir et al.

(10) Patent No.: US 9,386,990 B2
(45) Date of Patent: Jul. 12, 2016

(54) NERVE REPAIR WITH A HYDROGEL AND ADHESIVE (75) Inventors: David F. Muir, Gainesville, FL (US); James B. Graham, Silver Springs, FL (US); Debbie Neubauer, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 530 days.

(21) Appl. No.: 12/922,725

(22) PCT Filed: Mar. 19, 2009

(86) PCT No.: PCT/US2009/001739
§ 371 (c)(1),
(2), (4) Date: Feb. 18, 2011

(87) PCT Pub. No.: WO2009/117127
PCT Pub. Date: Sep. 24, 2009

(65) Prior Publication Data
US 2011/0137328 A1 Jun. 9, 2011

Related U.S. Application Data (60) Provisional application No. 61/070,130, filed on Mar. 19, 2008.

(51) Int. Cl.
*A61B 17/11* (2006.01)
*A61L 24/00* (2006.01)
(Continued)

(52) U.S. Cl.
CPC ......... *A61B 17/1128* (2013.01); *A61L 24/0031* (2013.01); *A61L 24/046* (2013.01);
(Continued)

(58) Field of Classification Search
CPC .. A61K 9/0024; A61K 9/0092; A61L 31/145; A61L 2430/32; A61L 26/008; A61L 27/52; A61L 24/00; A61L 24/0031; A61L 24/106; A61B 17/1128
USPC .......... 424/422, 423, 484, 486; 523/118, 113, 523/105, 114; 128/898; 606/152, 213; 530/354, 362
See application file for complete search history.

(56) References Cited

U.S. PATENT DOCUMENTS 4,586,504 A * 5/1986 de Medinaceli .............. 606/152
4,778,467 A * 10/1988 Stensaas et al. ........... 623/23.64
(Continued)

FOREIGN PATENT DOCUMENTS

WO    WO 93/16687    9/1993
WO    WO 00/051538    9/2000
WO    WO 02/39948 A2    5/2002

OTHER PUBLICATIONS

Deftereos, Maria et al., PEG Hydrogels as nerve guidance materials, 2003 Summer Bioengineering Conference, Jun. 25-29, Sonesta Beach Resort, Key Biscayne, FL, pp. 1115-1116.*

(Continued)

*Primary Examiner* — Christopher L Templeton
(74) *Attorney, Agent, or Firm* — Saliwanchik, Lloyd & Eisenschenk (57) ABSTRACT

The subject invention provides materials and methods for effective nerve repair. In a preferred embodiment, the subject invention provides nerve repair methods comprising the steps of applying a fibrin glue between severed nerve stumps, coapting the nerve stumps, and applying a polyethylene glycol (PEG) hydrogel to encase the coapted nerve stumps.

4 Claims, 8 Drawing Sheets

(51) Int. Cl.
  *A61L 24/04* (2006.01)
  *A61L 24/10* (2006.01)
  *A61L 27/18* (2006.01)
  *A61L 27/52* (2006.01)
  *A61L 31/14* (2006.01)

(52) U.S. Cl.
  CPC .............. *A61L 24/106* (2013.01); *A61L 27/18* (2013.01); *A61L 27/52* (2013.01); *A61L 24/00* (2013.01); *A61L 31/145* (2013.01); *A61L 2430/32* (2013.01)

(56) References Cited

U.S. PATENT DOCUMENTS

| | | | |
|---|---|---|---|
| 4,986,828 A * | 1/1991 | de Medinaceli | 606/152 |
| 5,011,486 A * | 4/1991 | Aebischer et al. | 623/1.15 |
| 5,733,563 A | 3/1998 | Fortier | |
| 5,972,371 A * | 10/1999 | Gilchrist et al. | 424/426 |
| 6,312,725 B1 * | 11/2001 | Wallace et al. | 424/484 |
| 6,730,299 B1 | 5/2004 | Tayot et al. | 424/45 |
| 6,911,227 B2 * | 6/2005 | Hubbell et al. | 427/2.14 |
| 7,057,019 B2 | 6/2006 | Pathak | |
| 7,319,035 B2 | 1/2008 | Vacanti et al. | |
| 2001/0031974 A1 | 10/2001 | Hadlock et al. | |
| 2003/0204197 A1 * | 10/2003 | Onyekaba et al. | 606/152 |
| 2004/0086493 A1 * | 5/2004 | Hubbell et al. | 424/93.7 |
| 2004/0121011 A1 * | 6/2004 | McKerracher | 424/468 |
| 2004/0170664 A1 * | 9/2004 | Spector et al. | 424/426 |
| 2004/0195710 A1 * | 10/2004 | Hubbell et al. | 264/4.1 |
| 2004/0267289 A1 * | 12/2004 | Cheng | 606/152 |
| 2005/0008632 A1 * | 1/2005 | Stimmeder | A61K 9/1647 424/94.64 |
| 2005/0214376 A1 * | 9/2005 | Faure et al. | 424/486 |
| 2006/0083734 A1 * | 4/2006 | Cheng et al. | 424/94.64 |
| 2006/0228416 A1 * | 10/2006 | Faure et al. | 424/486 |
| 2007/0100358 A2 | 5/2007 | Romero-Ortega et al. | |
| 2007/0269481 A1 * | 11/2007 | Li et al. | 424/423 |
| 2008/0107632 A1 * | 5/2008 | Cheng et al. | 424/93.7 |
| 2010/0297218 A1 * | 11/2010 | Gong et al. | 424/450 |

OTHER PUBLICATIONS

Nisbet et al, Neural tissue engineering of the CNS using hydrogels, Journal of Biomedical Materials Research Part B: Applied Biomaterials, vol. 87B, Issue 1, pp. 251-263, Oct. 2008-published Dec. 27, 2007.*

Fortier, G. et al., "High water content BSA-PEG hydrogel for controlled release device: Evaluation of the drug release properties," *Journal of Controlled Release*, 1996, pp. 177-184, vol. 38, Nos. 2-3.

Lore, A.B. et aL, "Rapid Induction of Functional and Morphological Continuity between Severed Ends of Mammalian or Earthworm Myelinated Axons," *The Journal of Neuroscience*, 1999, pp. 2442-2454, vol. 19, No. 7.

Bhandari, P.S., et al., "What is new in peripheral nerve repair?" *Indian Journal of Neurotrauma*, Jan. 1, 2007, Retrieved from the internet, http://www.sciencedirect.com/science/article/pii/S0973050807800061/pdf?md5=fb1b8592f90156e6 038e3.0836177ec21&pid=1-s2.0-S0973050807800062-main.pdf.

Chaikovskii, Yu B., et al., "Treat Damage Peripheral Nerve Surgical Intervening Wrap End Aqueous gel contain Quercetin Oral Administer," *Kiev Doctor Training Institute*, Nov. 15, 1994, Database WPI, EP-002715615, Thomson Scientific, London, GB.

Sarig-Nadir, Offra, et al., "Compositional Alterations of Fibrin-Based Materials for Regulating in Vitro Neural Outgrowth," *Tissue Engineering: Part A*, 2008, vol. 14, No. 3, p. 402-411.

Wei, Y., et al., "Application of Sodium Hyaluronate gel and autogenous vein wrapping in reducing the local scar hyperplasia at stoma," *Chinese Journal of Clinical Rehabilitation*, Nov. 14, 2005, vol. 9, No. 42, p. 75-77, Database Embase, XP-002715616, Elsevier Science Publishers, Amsterdam.

* cited by examiner

NERVE REPAIR WITH A HYDROGEL AND ADHESIVE

CROSS REFERENCE TO A RELATED APPLICATION

This application is a National Stage Application of International Application Number PCT/US2009/001739, filed Mar. 19, 2009; U.S. Provisional Patent Application Ser. No. 61/070,130, filed Mar. 19, 2008; which are incorporated herein by reference in their entirety.

BACKGROUND OF INVENTION

A nerve carries the peripheral processes (or axons) of neurons. The neuronal cell bodies reside in the spinal cord (motor neurons), in ganglia situated along the vertebral column (spinal sensory ganglia) or in ganglia found throughout the organs of the body (autonomic and enteric ganglia). A nerve consists of axons, Schwann cells and extensive connective tissue sheaths (Dagum A B (1998) *J Hand Ther* 11:111-117). The outer covering, the epineurium, is made of collagenous connective tissue that cushions the fascicles from external pressure and surrounds the perineurium. The perineurium surrounds the individual fascicles and, together with endothelial cells in the endoneurial microvessels, functions as the blood-nerve barrier. The endoneurium lies inside the perineurium and consists of collagenous tissue that surrounds the Schwann cells and axons. A fascicular group consists of two or more fascicles surrounded, respectively, by perineurium and epineurium. The topography of nerves is constant distally, with a group of fascicles being either sensory or motor. The neuron consists of a soma (cell body) and an axon, which can be several feet long.

Nerve injuries are a major source of chronic disability. Poor management of nerve injuries is associated with muscle atrophy and can lead to painful neuroma when severed axons are unable to reestablish continuity with the distal nerve. Although nerves have the potential to regenerate after injury, this ability is strictly dependent upon the regenerating nerve fibers making appropriate contact with the severed nerve segment. Regenerating axons that fail to traverse the gap or injury site and enter the basal lamina of the severed distal nerve segment will deteriorate, resulting in neuronal death, muscle atrophy and permanent functional deficit (Fawcett J W et al. (1990) *Annu Rev Neurosci* 13:43-60).

In nerve injuries where there is axonal disruption, but the continuity of the endoneurial sheath remains intact (e.g., crush injury), axons regenerate within their original basal lamina and complete recovery can be expected. In contrast, axonal regrowth may be severely compromised after nerve transection and surgical repair is highly dependent on the realignment of the nerve elements described above (Dagum A B (1998) *J Hand Ther* 11:111-117).

Numerous methods of nerve coaptation have been tested and applied, including various suture methods, adhesives, laser treatments, and conduits. Nerve repair with sutures is standard practice. The use of sutures provides a long-lasting union but has limitations and complications. For example, sutures can elicit a foreign body reaction, impair vascularity, and potentially disrupt axonal regeneration. Therefore, coaptation of severed nerves without sutures would be desirable and could potentially eliminate the tissue trauma associated with traditional suturing techniques.

A variety of sutureless nerve repair methods have been explored including the use of biological glues. The advantages of gluing techniques include the potential for simple application and rapid repair time. Coaptation by gluing has the potential to be more efficient, eliminate variables of tension due to suture placement and technique, and improve alignment of fascicles.

Fibrin glue has been tested most extensively as a biological adhesive. Unfortunately, fibrin glue has insufficient adhesive and tensile strength to ensure a secure nerve union for most nerve repairs. Fibrin glue repairs are prone to dehiscence (Cruz et al., 1986; Maragh et al., 1990) and mechanical testing shows it imparts negligible strength to a nerve coaptation (Temple et al., 2004). In addition to its lack of adhesive strength, fibrin glue is rapidly degraded and is completely absorbed within several days in vivo. Therefore, repair with fibrin glue alone is unreliable and rarely performed.

Several glues with high adhesive and tensile strength have been developed. Polyethylene glycol (PEG) based hydrogels have been explored in tissue repair applications. PEG-hydrogels bind strongly to tissues and act as effective sealants (Preul et al., 2003). PEG-hydrogels do not provide a good substrate for cell attachment and growth, and can have desirable effect on the inhibition of tissue-tissue adhesions that often occur after surgical repair (Hem et al., 1998). This same property indicates that PEG-hydrogels must be applied judiciously as to not interfere with cell migration required for tissue regeneration. PEG-hydrogels have been explored in neural tissue repair and reconstruction (Woerly, 1993). The main goal of these repair studies is to derivatize or otherwise alter the hydrogels to support cell adhesion. Hydrogels are marketed as sealants. A successful product, DuraSeal (Confluent Surgical, Inc.), is used to prevent the leakage of fluid from the dura after repair with sutures.

BRIEF SUMMARY

The subject invention provides materials and methods for effective nerve repair, wherein the methods utilize a hydrogel and, optionally, an adhesive to facilitate repair of coapted nerve elements. In a preferred embodiment, the subject invention provides nerve repair methods comprising the use of both an adhesive and a hydrogel to coapt severed nerve ends, either directly or via a nerve graft. In a specific embodiment exemplified herein, the adhesive is a fibrin glue and the hydrogel is a polyethylene glycol (PEG) hydrogel.

One method of the subject invention comprises coapting nerves with a PEG hydrogel alone. In a more preferred embodiment, the method of the subject invention comprises the application of a fibrin glue to the nerve interface followed by application of a PEG hydrogel to encase the nerve.

A PEG hydrogel can be formed by mixing two components, a PEG-based derivative and a cross-linking agent. When combined, these components form the PEG hydrogel. In one embodiment of the subject invention, these components are premixed and then used in the nerve repair method described herein. In another embodiment, the method of the subject invention comprises application of the PEG component to the nerve first, followed by the application of the cross-linking agent to form the hydrogel directly on the nerve. Other hydrogels can also be used as described herein. In preferred embodiments, the hydrogel encases the nerve and is non-permissive to nerve growth. Thus, re-growing axons are inhibited from pathological, dysfunctional, and/or inefficient growth.

In a preferred embodiment the method involves first joining the nerve ends (or nerve graft) with a fibrin glue. This holds the nerve ends in the desired position and affixes and/or seals the coaptation. Thereafter, the nerve repair is secured by secondary encasement with a hydrogel. The hydrogel can be formed by either of the two methods described above (as a premix of, for example, PEG and crosslinker or by a two step application of the PEG component followed by the crosslinking component).

A further aspect of the subject is a non-adhesive mold to contain and form the hydrogel. The subject invention further provides a backing or carrier that contains the hydrogel component(s) used to wrap the nerve during application.

BRIEF DESCRIPTION OF DRAWINGS

The file of this patent contains at least one drawing executed in color. Copies of this patent with color drawings(s) will be provided by the Patent and Trademark Office upon request and payment of the necessary fee.

DETAILED DISCLOSURE

The subject invention provides compositions and methods for promoting the repair and/or growth of nerve tissue. The compositions and methods of the subject invention can be employed to restore the continuity of nerves interrupted by disease, traumatic events or surgical procedures. The compositions and methods of the subject invention promote repair of nerve tissue by the growth of axons that successfully penetrate damaged nerve tissue or implanted nerve grafts, resulting in greater functional recovery.

Following peripheral nerve injury, if axons in the proximal stump are to regenerate and reinnervate their targets successfully, they need to select a pathway in which to grow. This process of pathway selection involves the navigation of regenerating axons in the proximal stump past, for example, a surgical repair site and into endoneurial tubes in the distal stump.

In a specific embodiment described more fully herein, a hydrogel can be applied according to the subject invention to the exterior of injured nerves to facilitate efficient nerve repair. In accordance with the subject invention, application of a hydrogel around the repair site of a cut peripheral nerve helps to direct functional axonal regeneration.

One method of the subject invention comprises coapting nerves with a PEG hydrogel alone. In a more preferred embodiment, the method of the subject invention comprises the application of fibrin glue to the nerve interface followed by application of a PEG hydrogel to encase the nerve.

Nerve repair with suture is associated with several complications that are reduced or eliminated by the use of the methods of the subject invention. These complications can include inflammation, fibrosis and scar formation. Also, the use of the materials and methods of the subject invention can reduce the misdirection and dysfunctional growth of axons that escape the nerve at the suture line. This not only improves nerve regeneration but also decreases the likelihood of neuropathies associated with aberrant growth including neuroma and dysaesthesia, paresthesia, the Tinel sign, chronic pain, and abnormal motor function.

Advantageously, the nerve coaptation methods of the subject invention provide the means to align and fix nerve components in place, without inducing compression or interfering with cellular and molecular processes in nerve regeneration. Additional advantages of the subject invention include providing a stronger and more permanent union between the nerve ends. This is accomplished by the application of a hydrogel, preferably in conjunction with a fibrin glue.

As discussed below, the materials and methods of the subject invention can be combined with other techniques for promoting nerve repair. These other techniques can include, for example, the application of enzymes such as chondroitin sulfate proteoglycan (CSPG) degrading enzymes and/or heparin sulfate (HSPG) degrading enzymes. These embodiments are discussed below.

The method of the subject invention can also reduce fibrotic scarring associated with nerve repair and regeneration. Advantageously, the use of a hydrogel reduces cell migrations into and out of the repair site. This is achieved by encasing and sealing the nerve coaptation with the hydrogel. In a preferred embodiment, these features are achieved by application of the hydrogel to reinforce and encase a coaptation initially established with a fibrin glue repair. The fibrin glue also prevents the hydrogel from entering into the repair site per se.

According to the methods of the subject invention, the hydrogel can be applied to a nerve-nerve coaptation (direct repair) and to nerve repair with an interpositional graft.

As used herein, the term "graft" refers to any tissue or tissue replacement intended for implantation within a human or animal. Various types of graft are encompassed within the subject invention, such as autografts, syngrafts, allografts, and xenografts. The size (e.g., length and diameter) of the graft is not critical to the subject invention. The graft may be a live (cellular) graft or a graft that has been rendered acellular, such as by chemical or thermal decellularization methods. The graft may be engineered from synthetic materials.

Hydrogels

In accordance with the present invention, a hydrogel is applied to hold a repaired nerve together. In a preferred embodiment, the hydrogel is a PEG-hydrogel. Advantageously, the PEG-hydrogel can be used to replace sutures. The hydrogel is formed around the nerve, adheres to the outside of the nerve, and holds the two nerve stumps securely in place thereby maintaining a tight apposition of the nerve stumps required for the repair process.

In accordance with the present invention, a hydrogel can be formed from a hydrogel precursor derived from any water soluble polymer including: polyoxyalkylenes, such as mono-poly(oxyalkylene)-substituted propylene glycol, di-poly(oxyalkylene)-substituted propylene glycol, mono-poly(oxyalkylene)-substituted trimethylene glycol, di-poly(oxyalkylene)-substituted trimethylene glycol, mono-poly(oxyalkylene)-substituted glycerol, di-poly(oxyalkylene)-substituted glycerol, and tri-poly(oxyalkylene)-substituted glycerol where the poly(oxyalkylene) can be poly(oxyethylene) or soluble poly(oxyethylene-co-oxypropylene); polyacrylates and polymethacrylates, such as poly(acrylic acid), poly(methacrylic acid), poly(hydroxyethylmethacrylate), poly(hydroxyethylacrylate), poly(methylalkylsulfoxide acrylates), poly(methylalkylsulfoxide methacrylates), and copolymers thereof; polyacrylamides and polymethacrylamides, such as poly(acrylamide), poly(methacrylamide), poly(dimethylacrylamide), poly(N-isopropylacrylamide), poly(N-(2-hydroxyethyl)methacrylamide), poly(N-(2-hydroxyethyl)acrylamide), poly(N-(2-hydroxypropyl)methacrylamide), poly(N-(2-hydroxypropyl)methacrylamide) and copolymers thereof; poly(N-vinyl lactam)s, such as poly(vinyl pyrrolidone), poly(vinyl caprolactam), and copolymers thereof; poly(vinyl alcohol); or naturally derived polymers, such as proteins, carboxylated polysaccharides, aminated polysaccharides, glycosaminoglycans, activated polysaccharides, alginic acid, pectinic acid, carboxy methyl cellulose, hyaluronic acid, heparin, heparin sulfate, chitosan, carboxymethyl chitosan, chitin, pullulan, gellan, xanthan, carboxymethyl starch, carboxymethyl dextran. Hydrogel precursors can be linear, branched, dendrimeric, hyperbranched, or star shaped polymers. The hydrogel precursor contains functionality for cross-linking by chemical, thermal or photochemical induced reactions.

For the purposes of the invention, the hydrogel precursor can be cross-linked to the hydrogel by formation of ionic or covalent bonds. The cross-linking can be promoted by the addition of a cross-linking reagent to the hydrogel. For example, the cross-linking reagent can be a di- or polyamine and the cross-linking functionality of the hydrogel can be a carboxylic acid or carboxylic acid derivative, for example, an ester, amide, acid anhydride, or imide. In addition to ionic cross-linking via an acid-base reaction, such as a carboxylic acid and an amine, ionic cross-linking can occur by ionic exchange between monovalent ions of the hydrogel precursor and polyvalent ions of the cross-linking reagent. Ionic cross-linking can occur by association of a polycationic or polyanionic hydrogel precursor with a complementary polyanionic or polycationic cross-linking reagent.

In one embodiment, the hydrogel used according to the subject invention is cross-linked with albumin. Materials, methods and procedures for forming and using hydrogels are known to those skilled in the art and can be found at, for example, U.S. Pat. Nos. 5,733,563 and 7,250,177, which are incorporated herein in their entireties.

Unlike the hydrogels used in other applications, the primary function of the hydrogel used according to the subject invention is not to act as a substrate for cell migration or tissue growth. Furthermore, in preferred embodiments, the hydrogel does not release or otherwise deliver an active agent. Also, the hydrogel is preferably non-immunogenic. Rather, the hydrogel encapsulates the nerve, holding the nerve elements in place facilitating axon regrowth and nerve regeneration while reducing aberrant cell migration and/or dysfunction axon regrowth.

Importantly, the hydrogel prevents the migration of cells and axons outside of the nerve proper. Thus, the PEG-hydrogel repels axons, inhibits them from exiting the nerve at the repair site and prevents axonal growth outside the nerve. In nerve repair aberrant cell migration contributes to loss of axons at the coaptation and is a significant clinical concern (Graham et al., 2007). This property (to prevent aberrant axonal growth) is a new discovery and novel use of hydrogel in nerve repair.

Adhesives

Optionally, the hydrogel can be applied to the injured nerve or nerve graft in conjunction with a tissue adhesive, such as a biological glue. Preferably, the biological glue is a fibrin-containing adhesive, such as fibrin glue, fibrin sealant, or platelet gel. As used herein, the terms "fibrin glue", "fibrin sealant", and "fibrin tissue adhesive" are used interchangeably to refer to a group of formulations containing fibrinogen and thrombin, which lead to the formation of a fibrin polymer at the site of application.

In accordance with a preferred embodiment of the subject invention, a fibrin glue is used to align nerve ends and to seal the coaptation at the time of nerve repair. Fibrin is applied to the face of the cut nerve elements. Because fibrin polymerizes slowly and with weak adhesion, fibrin glue allows the nerves to be positioned (and repositioned) until aligned satisfactorily over several minutes. Once in position the opposing nerve elements are held weakly in place by the fibrin glue union. A further advantageous aspect of the fibrin glue application is that it occupies the nerve-nerve interface and excludes a secondary adhesive (e.g. PEG hydrogel) from seeping between the coapted nerve elements. Thus, in accordance with the subject invention, fibrin glue can be applied to the nerve-nerve interface, not as an encasement, as in usual applications. Other types of "glues" can also be used. The important features of the glue is that, it can hold nerve elements together, at least temporarily, and it is permissive, or even conducive to nerve growth.

Although the use of fibrin glue is specifically exemplified herein, other adhesive can be used according to the subject invention. The adhesive should be capable of sufficient adhesion to facilitate alignment of nerve stumps and/or grafts and should be permissive of axon regrowth through these nerve structures. Such adhesives include, but are not limited to, alpha-2-antiplasmin, alpha-1-antitrypsin, alpha-2-macroglobulin, transglutaminase, aminohexanoic acid, aprotinin, a source of calcium ions, calcium alginate, calcium-sodium alginate, casein kinase II, chitin, chitosan, collagen, cyanoacrylates, epsilon-aminocaproic acid, Factor XIII, fibrin, fibrin glue, fibrinogen, fibronectin, gelatin, laminin, living platelets, methacrylates, PAI-1, PAI-2, plasmin activator inhibitor, plasminogen, platelet agonists, protamine sulfate, prothrombin, an RGD peptide, sphingosine, a sphingosine derivative, thrombin, thromboplastin, or tranexamic acid.

Advantageously, the biological properties of fibrin glue are particularly well suited for use within the nerve-nerve interface. First, it is rapidly degraded and cleared. Unlike other intended applications, rapid elimination of the fibrin is desirable in the method of the current invention. Its intended role typically ends within the timeframe of the surgical procedure. Second, prior to its degradation, fibrin provides a favorable substratum for cell migration and is readily infiltrated by nerve cells and regenerating axons. Therefore, the fibrin glue does not interfere with natural nerve repair processes.

Fibrin is a natural blood product and will appear at the site of nerve injury. Also, a fibrin clot contributes to nerve repair when a large gap exists. In this case, a fibrin clot or bridge can help reestablish nerve continuity. However, these properties are not critical in the present technology. Rather, fibrin is used as a biocompatible, transient adhesive that is permissive (not inhibitory) to nerve regrowth. The most important property is fibrin's ability to temporarily (for several minutes) hold the nerve stumps in position and to physically occupy the nerve-nerve interface, preventing seepage of a secondary adhesive.

CSPG-Degrading Enzymes

In one embodiment, CSPG-degrading enzymes are applied to the site of nerve repair. For example, the CSPG-degrading enzymes can be applied to the site of primary nerve repair involving coaptation of severed or trimmed nerve (i.e., end-to-end nerve coaptation).

The CSPG-degrading enzyme can be, for example, chondroitinase, hyaluronidase, and matrix metalloproteinase (MMP), or combinations thereof. In a further embodiment, the CSPG-degrading enzyme can be selected from the group consisting of chondroitinase ABC, chondroitinase A, chondroitinase C, chondroitinase AC, hyaluronidase, MMP-2, and MMP-9, or combinations thereof. The teachings of WO 2003/015612 A3 are incorporated herein in their entirety.

HSPG-Degrading Enzymes

In a further embodiment of the subject invention, HSPG-degrading enzymes can be applied to the site of nerve repair. For example, the HSPG-degrading enzymes can be applied to the site of primary nerve repair involving coaptation of severed or trimmed nerve (i.e., end-to-end nerve coaptation).

The HSPG-degrading enzymes used according to the subject invention can be human, animal, or bacterial in origin, naturally occurring or recombinant. The teachings of US-2003-0072749-A1; US-2003-0077258-A1; US-2003-0040112-A1; US-2004-0180434-A1; WO 2005/074655 A2 and WO 2003/015612 A3 are hereby incorporated herein by reference in their entirety.

In addition to one or more CSPG-degrading enzymes and/or HSPG-degrading enzymes, the subject invention can further comprise applying other biologically or pharmacologically active molecules, such as growth factors. Such growth factors include, but are not limited to, nerve growth factor (NGF), fibroblast growth factors (FGF-1 and 2), epidermal growth factor (EGF), ciliary neurotrophic factor (CNTF), brain derived neurotrophic factor (BDNF), neurotrophin-3, -4, and -5 (NT-3, -4, and -5), insulin-like growth factor-I and -II (IGF-I, II), transforming growth factor (TGF), glial growth factor-2 (GGF-2), vascular endothelial growth factor (VEGF), granulocyte-macrophage colony stimulating factor (GM-CSF), and lymphocyte infiltrating factor/cholinergic differentiating factor (LIF/CDF). Such molecules can be obtained naturally or by recombinant DNA techniques. Fragments or variants of such molecules that retain their biological or pharmacological activities can also be used. It is not intended that the hydrogel function primarily as a carrier or release vehicle for the delivery of adjunctive agents. Rather, the adjunctive agents can be used in conjunction with the hydrogel and their effectiveness enhanced by the ability of the hydrogel to limit their diffusion from the coaptation site.

Materials and Methods

Materials

DuraSeal was used as a prototype PEG-hydrogel. It has the desired biological properties but not the ideal physical ones. DuraSeal is a water soluble, PEG-hydrogel. DuraSeal is broken down and resorbed slowly, persisting in vivo for 1-2 months. DuraSeal is sold for use in a double-barrel syringe applicator. As designed, the two components are dissolved into water, and mixed by injection through the applicator. Once applied, it forms a flexible hydrogel sealant within 2-3 seconds. From the applicator it polymerized far too rapidly for practical use in this study. Instead, the components were hydrated, the PEG component applied first to the nerve surface and then the catalyst component was added to initiate polymerization. This overcame the problems encountered with the almost instantaneous polymerization of the hydrogel, which prevented controlled application and distribution to the nerve repair.

Fibrin glue products are available in numerous proprietary forms; most use double-barrel applicators to mix the two components at time of use. Here, fibrin glue was made from individual reagents, by mixing in equal parts of 95 mg/ml Fibrinogen and 500 U/ml Thrombin containing calcium chloride (Menovsky and Bartels, 1999).

Methods of Nerve Repair

Adult male Fisher rats were deeply anesthetized with isoflurane. Sciatic nerve for repair was isolated and transected with Biemer scissors at mid-thigh. Three repair methods were evaluated: 1) conventional epineurial suture (n=4), 2) PEG-hydrogel encasement (n=6), 3) fibrin glue followed by PEG-hydrogel encasement (n=6).

Suture repair. The proximal and distal stumps were immediately coapted using 9-0 sutures (epineurial on either side of nerve). If sciatic nerve was bifurcated into two individual branches, each branch was coapted with 1 suture through the face of each branch. No fibrin glue was used.

Sutureless repair with Duraseal. A sheet of non-stick film was placed under the nerve stumps. The two nerve ends were brought together, aligned, and held with forceps. The PEG component (as a viscose solution) was spread onto the nerve coaptation and margins (2.5 mm in each direction). Then the catalyst solution was applied. The hydrogel was allowed to fully polymerize for 2 min. The nerve and hydrogel encasement were released from the supporting film (also serving as a mold). The wound was closed.

Sutureless repair with fibrin glue and Duraseal. A sheet of non-stick film was placed under the nerve stumps. Fibrinogen solution was dabbed onto the faces of both nerve stumps. Thrombin solution was dabbed onto one of the nerve faces and the nerve stumps were aligned and held in place for 60 seconds until secure. The forceps were removed and fibrin glue allow to polymerize completely without additional manipulation for an additional 2 minutes. Next, the PEG component (as a viscose solution) was spread onto the nerve coaptation and margins (2.5 mm in each direction). Then the catalyst solution was applied. The hydrogel was allowed to fully polymerize for 2 min. The nerve and hydrogel encasement were released from the supporting film (also serving as a mold). The wound was closed.

Following are examples which illustrate procedures for practicing the invention. These examples should not be construed as limiting. All percentages are by weight and all solvent mixture proportions are by volume unless otherwise noted.

EXAMPLE 1

Figure 1:
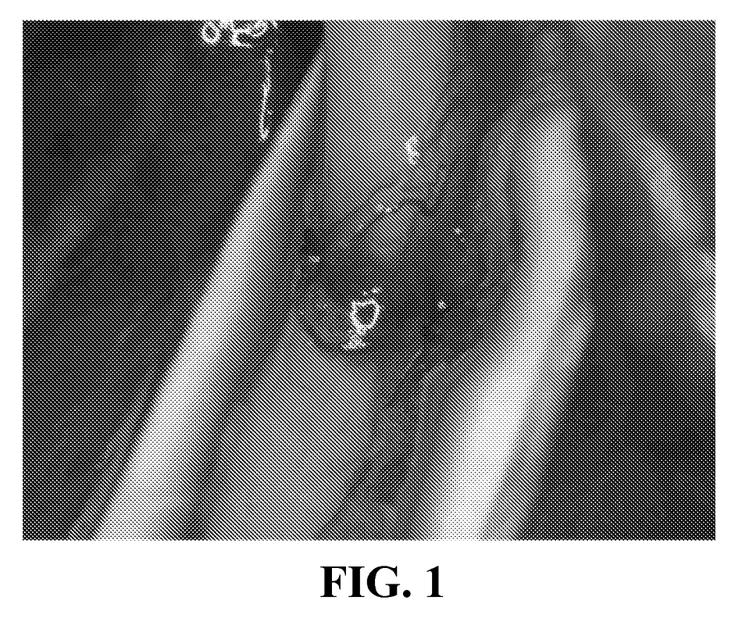
FIG. 1 shows a conventional epineurial suture nerve repair.
Figure 2:
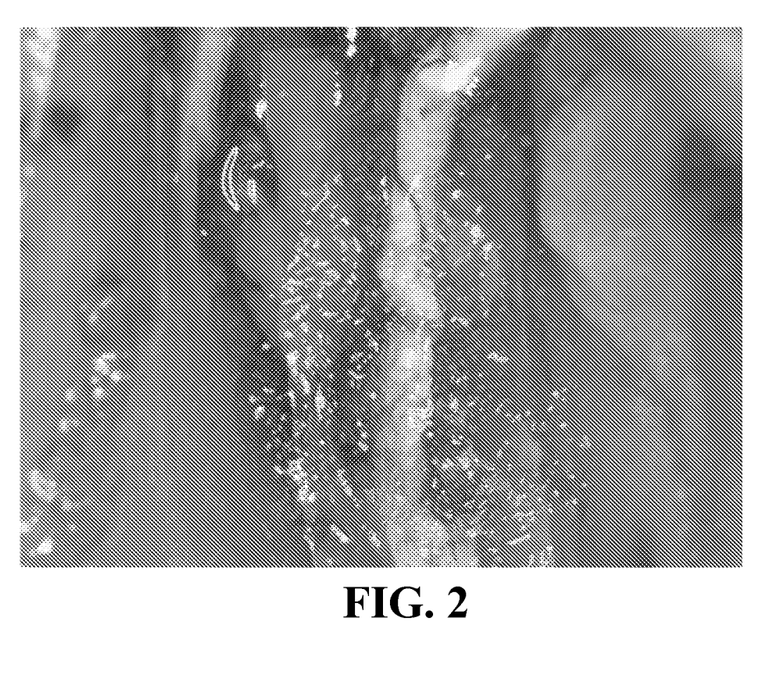
FIG. 2 shows nerve repair with hydrogel encasement alone. The hydrogel has a blue dye.

Nerve alignment with suture was good, but complicated as usual. Once the sutures were pulled taut, the nerve interface became partially misaligned and in places compressed (FIG. 1). In the hydrogel alone condition, the nerve stumps were held in place with forceps when applying the hydrogel components. This did not allow for much repositioning as the hydrogel polymerized rapidly. A goal was to avoid having the hydrogel seep between the nerve faces, so any repositioning was avoided (FIG. 2).

Figure 3:
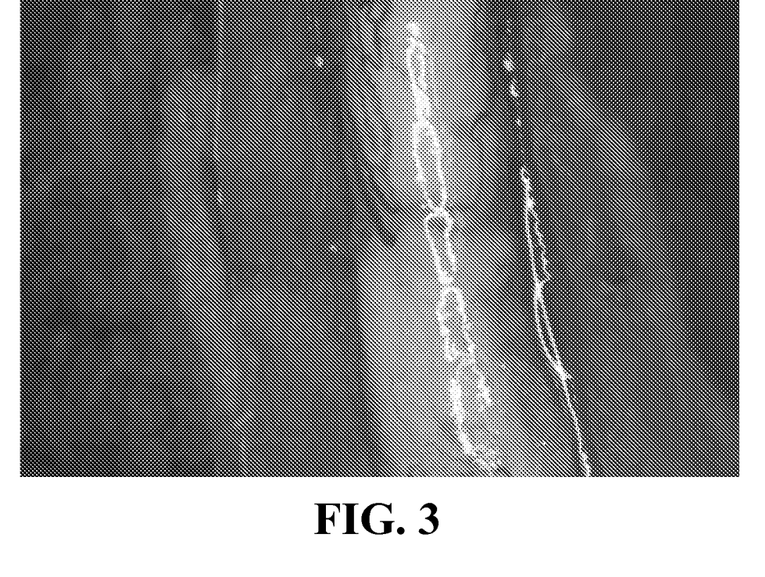
FIG. 3 shows nerve coaptation after the fibrin glue step (in repair with fibrin glue and hydrogel).
Figure 4:
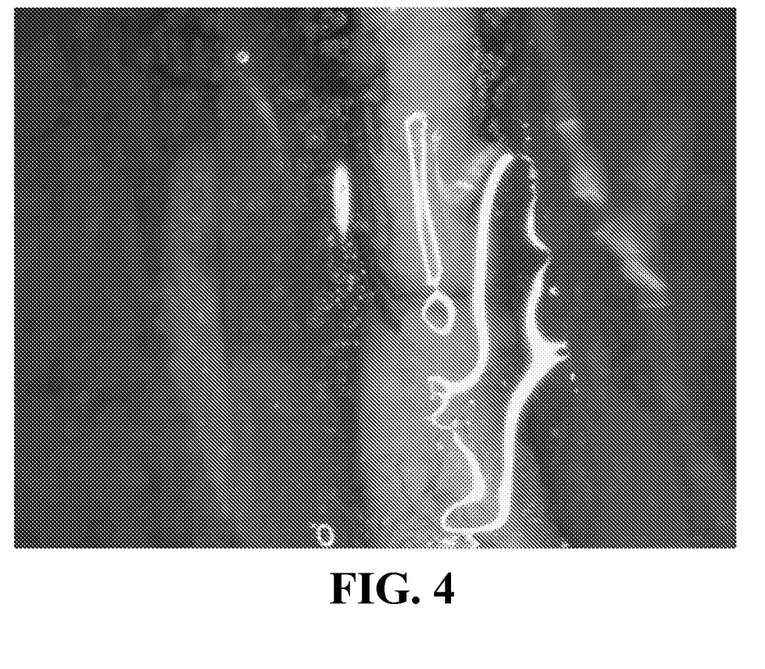
FIG. 4 shows nerve repair completed with fibrin glue and hydrogel.

In repair with fibrin glue and hydrogel, the fibrin glue step allowed for accurate alignment once applied (FIG. 3). The positioning was adjusted until satisfactory and the nerve was easily held in that position with forceps until the fibrin glue had polymerized sufficiently. This positioning was maintained and simplified the secondary application hydrogel encasement (FIG. 4).

Figure 5:
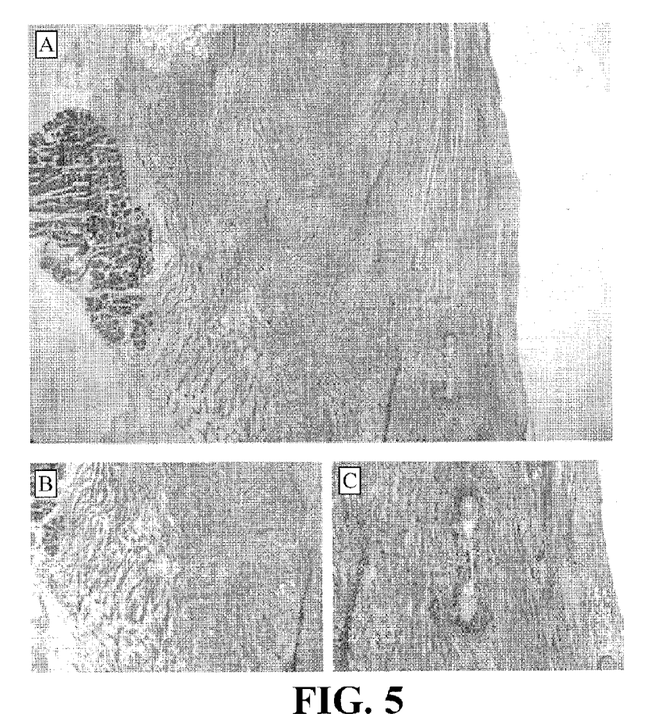
FIG. 5A-C show histology (H&E stain) of nerve repair with suture. Higher magnifications show axon snarls (5B, left) and foreign body reaction surrounding suture (5C, right).
Figure 6:
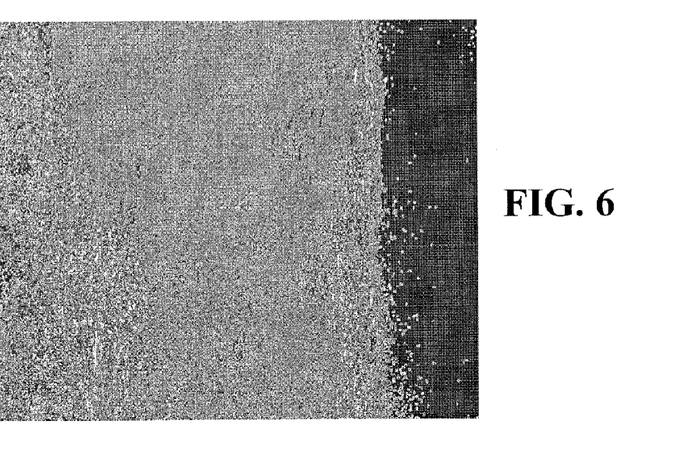
FIG. 6 shows laminin immunstaining of nerve repaired with sutures. Laminin stains the sheaths (which appear as tubes) that guide axons. These tubes are disrupted and mangled around the sutures. Blood vessels are also stained (which appear as rings, as seen on the right margin).

Histology was performed 3 weeks after nerve repair. Nerves repaired with suture showed the usual signs of compression and nerve extrusion (FIG. 5). Gross nerve continuity was achieved, although axons were found snarled at the coaptation. A usual foreign body reaction and hypercellularity was found around the sutures. Laminin immunostaining showed the contorted path of axons and undesirable lateral axon growth indicative of axons exiting the nerve at the suture line (FIG. 6).

Figure 7:
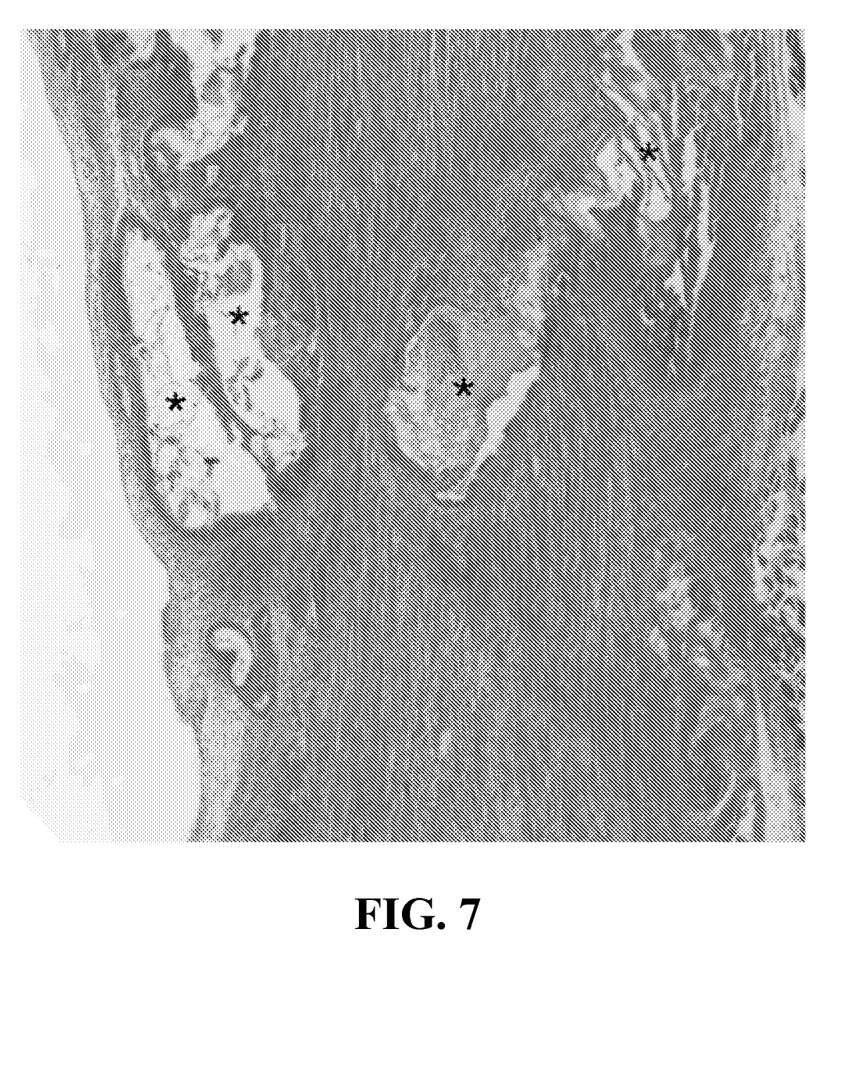
FIG. 7 shows nerve repair with PEG-hydrogel alone. When applied to the nerve repair directly the hydrogel seeped into the coaptation. Hydrogel pockets (asterisks) interfered and diverted axonal growth.
Figure 8:
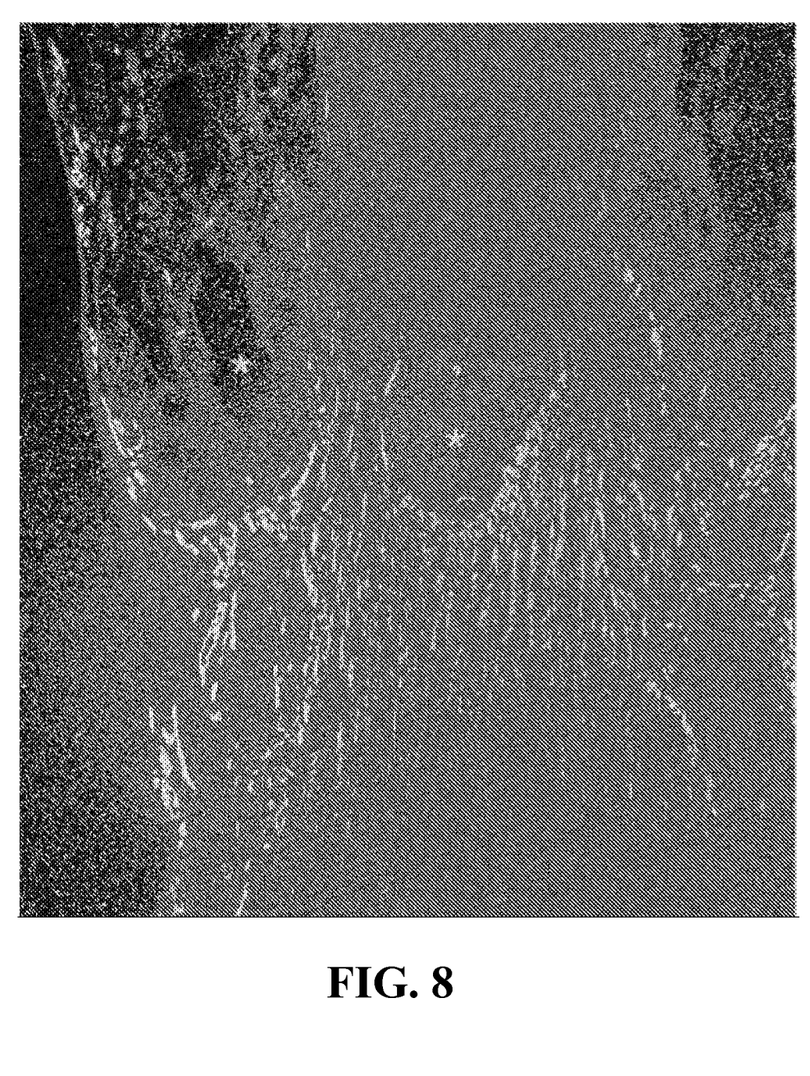
FIG. 8 shows nerve repair with PEG-hydrogel alone. Lamin immunstaining shows the nerve sheaths surrounding axons. These tubes are disrupted and mangled around the hydrogel pockets (asterisks).

Nerves repaired with the hydrogel alone showed the hydrogel solution had seeped into the nerve coaptation. This resulted in hydrogel pockets within the nerve. The hydrogel pockets and encasement around the nerve were clearly intact at 21 days after application. The hydrogel pockets greatly disrupted nerve continuity (FIG. 7). Also, there was little cellular infiltration into the hydrogel pockets. The hydrogel pockets did not appear to be toxic but induced an inflammatory response similar that seen with other inert foreign bodies (such as sutures). The hydrogel pockets clearly interrupted the linearity of nerve regeneration and misrouted axons throughout the coaptation region (FIG. 8.)

Figure 9:
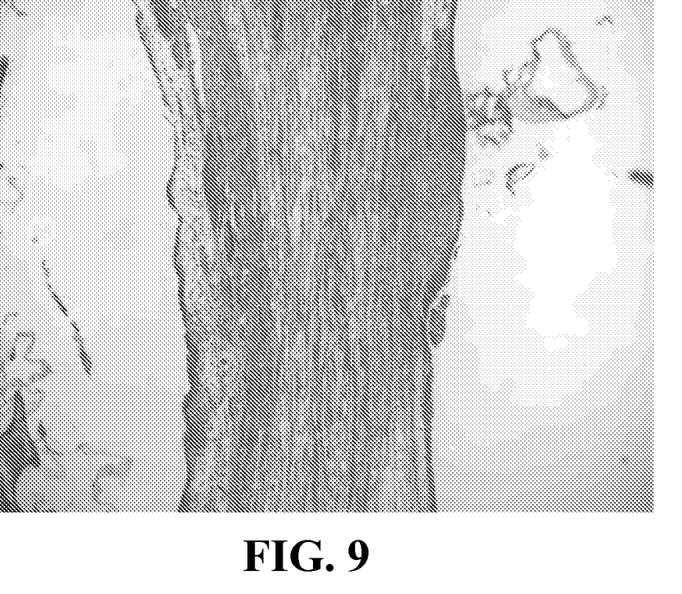
FIG. 9 shows nerve repair with fibrin glue alignment and PEG-hydrogel encasement. The coaptation interface is hardly distinguishable and excellent continuity was achieved.
Figure 10:
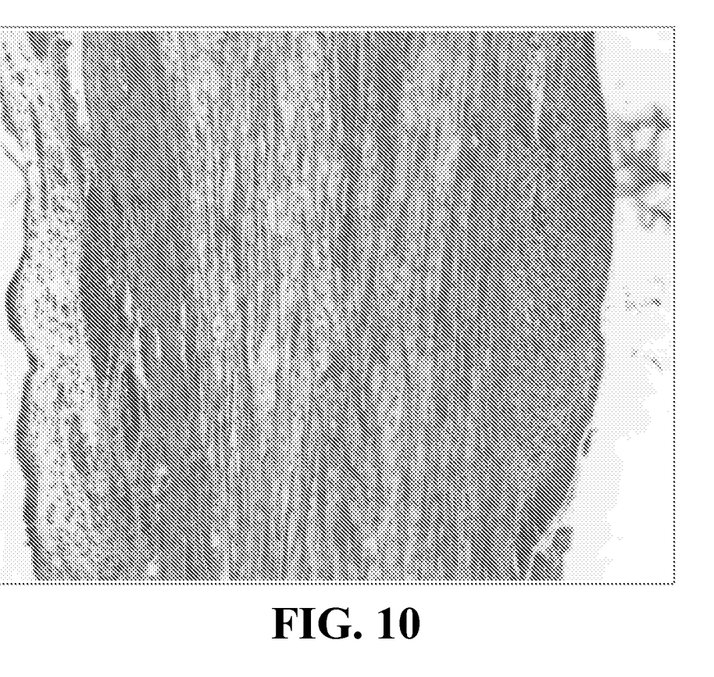
FIG. 10 shows nerve repair with fibrin glue alignment and PEG-hydrogel encasement. Axonal growth is highly linear and longitudinal with few interruptions. The outer nerve sheath is well healed and continuous.
Figure 11:
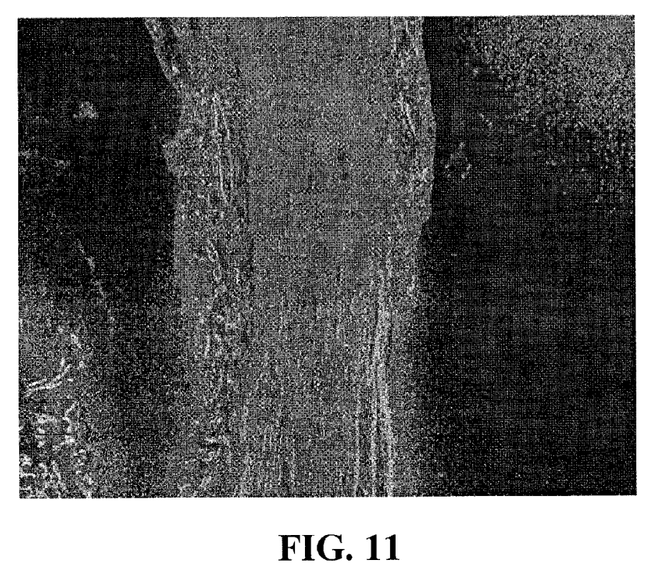
FIG. 11 shows nerve repair with fibrin glue alignment and PEG-hydrogel encasement. Laminin immunolabeling shows the linearity of basal lamina sheaths surrounding axons. Numerous blood vessels are found in the outer nerve margins indicating high continuity across the repair site.

Nerves repaired with fibrin glue and hydrogel showed excellent continuity. In most cases the nerve-nerve interface was difficult to pinpoint without high magnification. The hydrogel encasement remained intact at 21 days and had a connective tissue capsule on its outer surface, thereby preventing encapsulation of the nerve itself and adhesions with surrounding tissues (FIG. 9). There were no signs of compression or nerve extrusion. Axonal growth was very linear and directed on the longitudinal axis. There were no signs of abnormal axonal growth or fibers exiting the nerve at the repair site. The usual hypercellularity within the nerve evident, as was revascularization within the epineurial compartment. The outer nerve sheath was well-healed and continuous (FIGS. 10 and 11).

Figure 12:
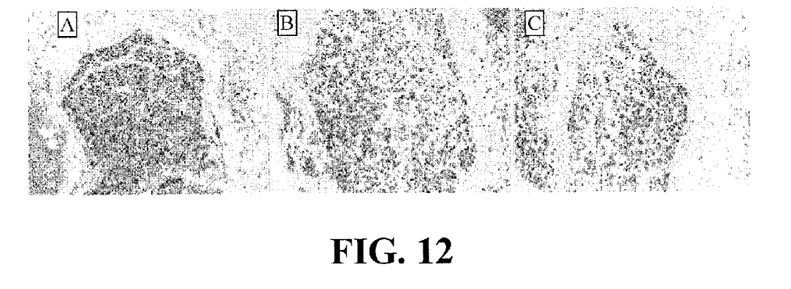
FIG. 12A-C shows axonal growth distal to the repair. Nerve repair with (A) suture, (B) PEG-hydrogel alone, and (C) fibrin glue alignment and PEG-hydrogel encasement. Sections were immunostained for neurofilaments to label axons. Numerous axons were observed in all three repair conditions.
Figure 13:
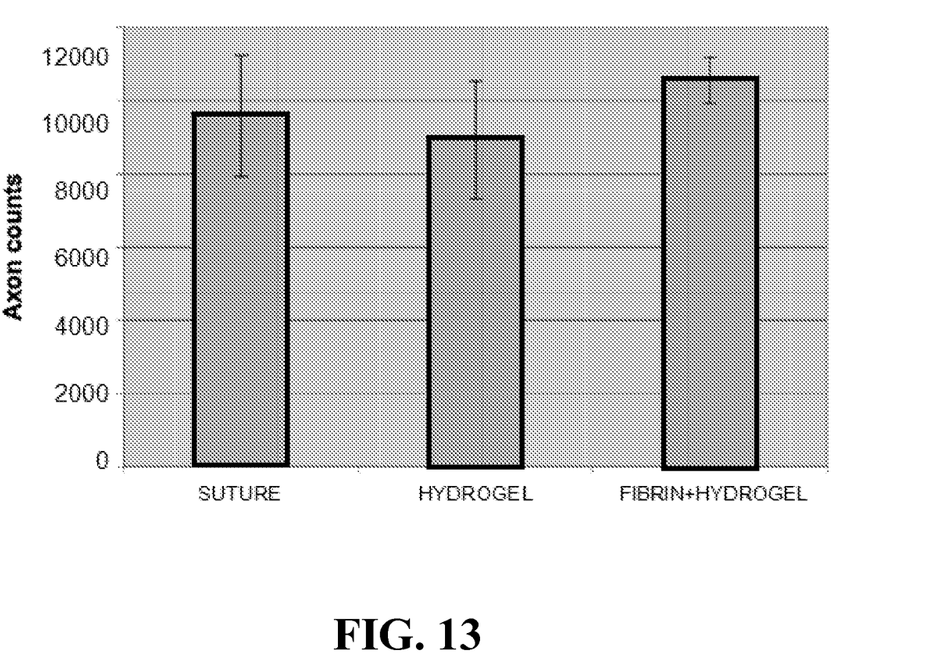
FIG. 13 shows axonal growth was scored distal to the repair. Axons were immunolabeled as described in FIG. 12 and counted by semi-automated image analysis software. Axon counts in the three repair conditions were not significantly different.

Section of the nerves 5 mm to the repair were immunolabeled for neurofilament to demonstrate regenerated axons. Axonal growth was robust in all three repair conditions (FIG. 12). The mean number of axons that had regenerated in the suture repair condition was 9,582±1654. The mean axon count with hydrogel alone was 8,925±1 607 and for fibrin glue+hydrogel was 10,553±673 (FIG. 13). With the relatively small study sample there was no significant differences between groups. There was a trend that the fibrin glue+hydrogel repair improved nerve regeneration. It is notable that the variation in this condition was less than half of that for the other repair conditions. This alone has important implications for reliability in clinical nerve repairs.

In summary, the fibrin glue plus hydrogel repair method compared favorably to conventional repair with suture. Repair with fibrin glue plus hydrogel was easy and effective. This method provided for excellent nerve continuity and did not cause interference in axonal growth associated with sutures or hydrogel alone. Thus, based on these findings, nerve repair with fibrin glue alignment and PEG-hydrogel encasement is a highly effective and operative alternative to conventional nerve repair with suture.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

REFERENCES

Watchmaker G P, Mackinnon S E. Advances in peripheral nerve repair. Clin Plast Surg 1 997; 24:63-73
Cruz N I, Debs N, Fiol R E. Evaluation of fibrin glue in rat sciatic nerve repairs. Plast Reconstr Surg 1986; 78:369-73.
Maragh H, Meyer B S, Davenport D, Gould J D, Terzis J K. Morphofunctional evaluation of fibrin glue versus microsuture nerve repairs. J Reconstr Microsurg 1990; 6:331-337
Preul et al. Toward optimal tissue sealants for neurosurgery: use of a novel hydrogel sealant in a canine durotomy repair model. Neurosurgery 2003; 53(5):1189-98
Temple C L, Ross D C, Dunning C E, Johnson J A. Resistance to disruption and gapping of peripheral nerve repairs: an in vitro biomechanical assessment of techniques. J Reconstr Microsurg 2004; 20:645-650.
Hern D L, Hubbell J A. Incorporation of adhesion peptides into nonadhesive hydrogels useful for tissue resurfacing. J Biomed Mater Res 1998; 39:266-276.
Woerly S. Hydrogels for neural tissue reconstruction and transplantation. Biomaterials 1993; 14:1056-1058.
Graham J B, Neubauer D, Xue Q S, Muir D. Chondroitinase applied to peripheral nerve repair averts retrograde axonal regeneration. Exp Neurol 2007; 203:185-1 95.
Menovsky T, Bartels R H. Stabilization and accurate trimming of nerve ends: practical use of fibrin glue: technical note. Neurosurgery 1999; 44:224-225.

We claim:

1. A method for nerve repair wherein said method comprises surgically coapting a partially or completely severed peripheral nerve, wherein nerve ends, each with a face and an exterior, have been created by the partial or complete severing of the peripheral nerve, and wherein said method comprises:
(a) applying a biological adhesive to the nerve faces; then
(b) coapting said nerve ends such that the nerve faces and biological adhesive are joined together to form an interface; and then
(c) forming a hydrogel at the exterior of the nerve ends, and not at the faces of the nerve ends, in order to encase the coapted nerve ends,
wherein the hydrogel comprises a hydrogel precursor and a cross-linking reagent that react via a chemical crosslinking reaction to form the hydrogel, wherein the step of forming the hydrogel comprises applying the hydrogel precursor and the cross-linking reagent only onto the exterior of the nerve ends at the coaptation nerve ends and not between the nerve ends, to catalyze the chemical crosslinking reaction to form the hydrogel; and wherein the adhesive is a fibrin glue.

2. The method, according to claim 1, wherein the hydrogel is a polyethylene glycol (PEG) hydrogel.

3. The method, according to claim 1, wherein the nerve is a human nerve.

4. The method, according to claim 1, wherein the adhesive is not aprotinin.

* * * * *